(12) United States Patent
Ross et al.

(10) Patent No.: US 7,787,948 B2
(45) Date of Patent: Aug. 31, 2010

(54) ENERGY EFFICIENT THERAPEUTIC PULSE GENERATOR SYSTEM

(76) Inventors: Robert A. Ross, 135 Apple La., Charlottesville, VA (US) 22903; Josef K. Hudson, 146 A Buckingham Cir., Charlottesville, VA (US) 22903

( * ) Notice: Subject to any disclaimer, the term of this patent is extended or adjusted under 35 U.S.C. 154(b) by 1050 days.

(21) Appl. No.: 11/336,891

(22) Filed: Jan. 23, 2006

(65) Prior Publication Data
US 2006/0167512 A1 Jul. 27, 2006

Related U.S. Application Data

(60) Provisional application No. 60/645,181, filed on Jan. 21, 2005.

(51) Int. Cl.
*A61N 1/36* (2006.01)
(52) U.S. Cl. ......................................................... 607/8
(58) Field of Classification Search ................... 607/28
See application file for complete search history.

(56) References Cited

U.S. PATENT DOCUMENTS

| 3,411,507 | A | 11/1968 | Wingrove et al. |
|---|---|---|---|
| 4,921,481 | A | 5/1990 | Danis et al. |
| 5,188,104 | A | 2/1993 | Wernicke et al. |
| 5,197,491 | A | 3/1993 | Anderson et al. |
| 5,292,344 | A | 3/1994 | Douglas et al. |
| 5,423,872 | A | 6/1995 | Cigaina et al. |
| 5,690,691 | A | 11/1997 | Chen et al. |
| 5,836,977 | A * | 11/1998 | Myers ........................... 607/5 |
| 6,096,063 | A * | 8/2000 | Lopin et al. ..................... 607/8 |
| 6,243,607 | B1 | 6/2001 | Mintchev et al. |
| 6,449,511 | B1 | 9/2002 | Mintchev et al. |
| 2005/0090868 | A1* | 4/2005 | Cansell ........................... 607/5 |

* cited by examiner

*Primary Examiner*—Scott M Getzow
*Assistant Examiner*—Amanda Patton
(74) *Attorney, Agent, or Firm*—Sheldon H. Parker

(57) ABSTRACT

The present invention relates generally to a therapeutic pulse generator system used to provide energy efficient stimulation/pacing by causing controlled cellular depolarization based on pre-measured charge transfer. This is accomplished by periodic electrical characterization of the electrode-tissue interface. Each channel of stimulation is programmed individually enabling the clinician to customize the therapeutic protocol. Energy efficiency may also be further improved through the use of a multi-channel lead in which the amount of energy required for each subsequent channel may be set to be less than the previous channel. The total energy required for multi-channel stimulation/pacing has also been shown to be less than that required by a single channel for the same therapeutic benefit.

8 Claims, 11 Drawing Sheets

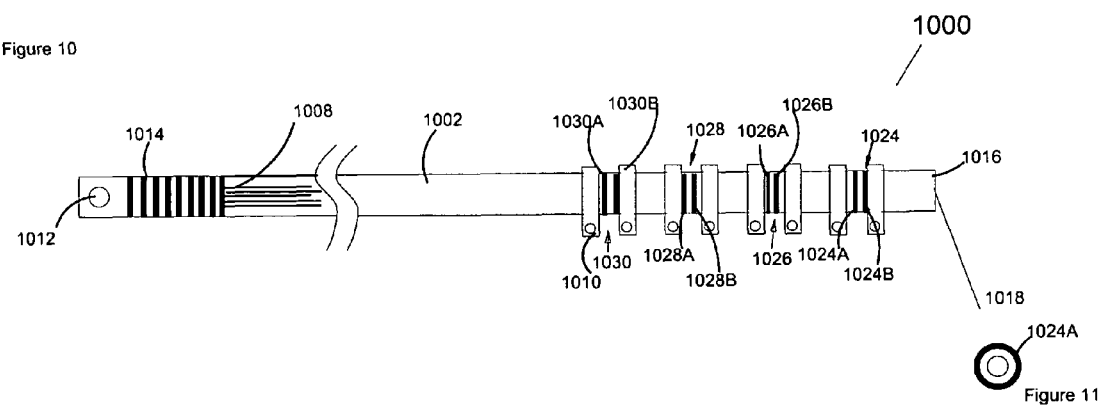
Figure 10
Figure 11
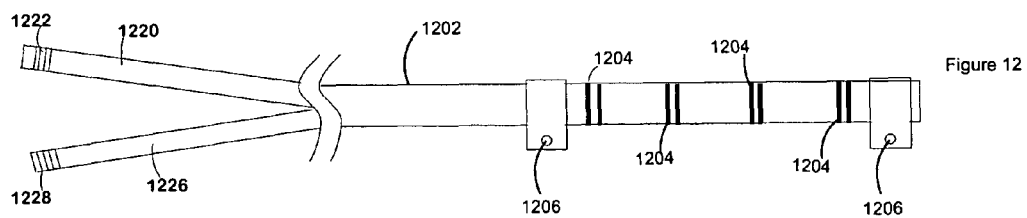
Figure 12

ENERGY EFFICIENT THERAPEUTIC PULSE GENERATOR SYSTEM

BACKGROUND

1. Field of the Invention

The present invention relates generally to a therapeutic pulse generator system used to provide energy efficient stimulation/pacing by causing controlled cellular depolarization based on pre-measured charge transfer and is accomplished by periodic electrical characterization of the electrode-tissue interface.

2. Related Art

Material, in the form of edible food and liquids, is directed through the organs in the gastrointestinal (GI) tract via peristaltic movement. The timing of the contractions of each of the organs is controlled by a physiological mechanism. The gastric "slow wave" in the normal human stomach, which regulates the contraction propagation frequency in the stomach, is reported to be approximately three cycles per minute. Other organs in the GI tract normally have different propagation frequencies. For example, it is believed that the frequency at the top of the duodenum is approximately 12.5 cycles/minute, and the frequency more distally in the small bowel, is approximately 9 cycles/minute (cpm).

Abnormalities in myoelectric activity in the GI tract may result in a variety of disorders harmful to human subjects. For example, gastroparesis exists when a patient experiences delayed gastric emptying. Conversely, dumping syndrome and some diarrhea states may be caused by gastric emptying which is too quick. Constipation results when the colon fails to move fecal matter properly. By contrast, chronic dumping syndrome, short bowel syndrome, and idiopathic diarrhea may be the result of the colon moving matter too quickly. Table 1 identifies a number of different clinical conditions which result from irregular gastric and intestinal myoelectric activity.

Pacemakers have been used for many years in cardiac care. These devices are typically implantable, and include control circuitry and electrodes that stimulate the heart tissue on a regimented basis. Pacemakers have been suggested for use in pacing the stomach; however, the level of understanding of stomach pacing is not as well developed as cardiac pacing. In addition, the requirements for effective stomach pacing are quite different from those for cardiac pacing. Ideally, a gastric pacemaker should deliver electrical signals to entrain natural gastric function.

U.S. Pat. No. 5,690,691 to Chen et al discloses a portable or implantable gastric pacemaker includes multiple electrodes that are positionable on the inner or outer surface of an organ in the gastro-intestinal tract and which are individually programmed to deliver a phased electrical stimulation to pace peristaltic movement of material through the GI tract. The pacemaker will accommodate variations in stimulation pulse amplitudes, stimulation pulse durations, stimulation pulse periods, and relative stimulation pulse phasing among the electrodes. Computer control may be used to adjust and vary all stimulation parameters delivered by the electrodes to achieve effective treatment and re-training of an organ for natural pacing. The pacemaker may be programmed with parameters to enhance or accelerate peristaltic movement through the gastric tract or to attenuate the peristaltic movement to treat such conditions eating disorders or diarrhea.

U.S. Pat. No. 3,411,507 to Wingrove discloses a device for gastrointestinal stimulation which uses an electrode positioned on a nasogastric catheter and an electrode secured to the abdominal wall. In operation, the nasogastric catheter is inserted into the patient's stomach. To institute peristaltic activity, the patient is preferably given an electrical stimulation for the first five seconds of every minute until positive results are obtained. The electrical stimulation is for a period of 0.1 milliseconds (ms) every 25 ms of the first five minutes. Wingrove also discloses using electrical stimulation of the same order of magnitude as the normal range of periodicity of the inherent peristaltic pacemaker action of the duodenum. The stimulation process is discontinued after the first bowel movement. Wingrove suffers from the disadvantage of only being a short term device. That is, it is only useful for patients in a hospital setting, and particularly patients that are laying down. Wingrove offers no long term solution to patients with digestive disorders. In addition, Wingrove does not allow for adjusting the electrical stimulation to suit the needs of a particular patient.

U.S. Pat. No. 5,292,344 to Douglas discloses a percutaneously placed electrical gastrointestinal pacemaker which provides for stimulation, sensing, delivery of fluids and nutrients, and pH sensing. The Douglas device may be used to treat a wide variety of gastric disrhythmias and may be used for both short and long term patient care. In operation, a plurality of electrodes are percutaneously and endoscopically placed on the inner lining of the gastrointestinal tract. The electrodes are all simultaneously pulsed with the same current and stimulation pulse rate. The current and stimulation pulse rate are adjustable by both mechanical and electrical systems. A pH sensor and a pressure sensor are connected inside the stomach, and are used for analysis of the electrical stimulation effects. Control circuitry is used in a feedback loop to control the timing of stimulation pulses. For example, if a response to the electrical stimulation is delayed beyond a controllable time threshold, a signal is given to provide another stimulative pulse. In addition, the control circuitry may be used to uniformly adjust the strength of the stimulation pulse, and to alert primary care providers of possible dangers. The Douglas gastric pacemaker provides several advantages. First, it is portable, and may be worn by a patient during day-to-day activities. Second, it allows for long term pacing. Third, it provides multiple electrodes and feedback elements. However, the Douglas system requires intense signals to be delivered to one region of the stomach, and does not address destructive interference problems which may occur when multiple sites are stimulated simultaneously.

Several other U.S. patents show the use of electrical stimulation of organs. For example, U.S. Pat. No. 5,188,104 to Wernicke et al. discloses stimulation of the vagus nerve for the treatment of eating disorders such as compulsive overeating, bulimia, or anorexia nervosa. Wernicke et al. does not discuss the treatment of gastric motility disorders or the restoration of normal gastric peristalsis. U.S. Pat. No. 5,423,872 to Cigaina discloses stimulating a single electrode pair affixed to the stomach for the purpose of decreasing the frequency of the gastric slow wave. The Cigaina device is used for treating obesity and other over eating disorders. U.S. Pat. No. 4,921,481 to Danis is related to a process for monitoring the frequency of gastric myoelectric signals to aid in the correct placement of gastric feeding tubes. U.S. Pat. No. 5,197,491 to Anderson describes a technique for placing an electrode into a patient's stomach adjacent to the heart for cardiac stimulation. U.S. Pat. Nos. 6,243,607 and 6,449,511 to Mintchev describe gastrointestinal pacemakers with both fixed and variable stimulus. Neither patent correctly references the essential link between entrainment of the gastric slow wave and improvement of gastric motility disorders. None of the aforementioned patents describe the use of energy efficient load characterization and predetermined charge based stimulation technique described herein.

BRIEF DESCRIPTION OF THE DRAWINGS

The invention will be described in conjunction with the accompanying drawings, in which:

FIG. 10 is a top view of the disclosed multi-channel lead of the instant invention;

FIG. 11 is a side view of a multi-channel pacing lead;

FIG. 12 is a top view of an alternate embodiment of a multi-channel lead;

DETAILED DESCRIPTION

Figure 1:
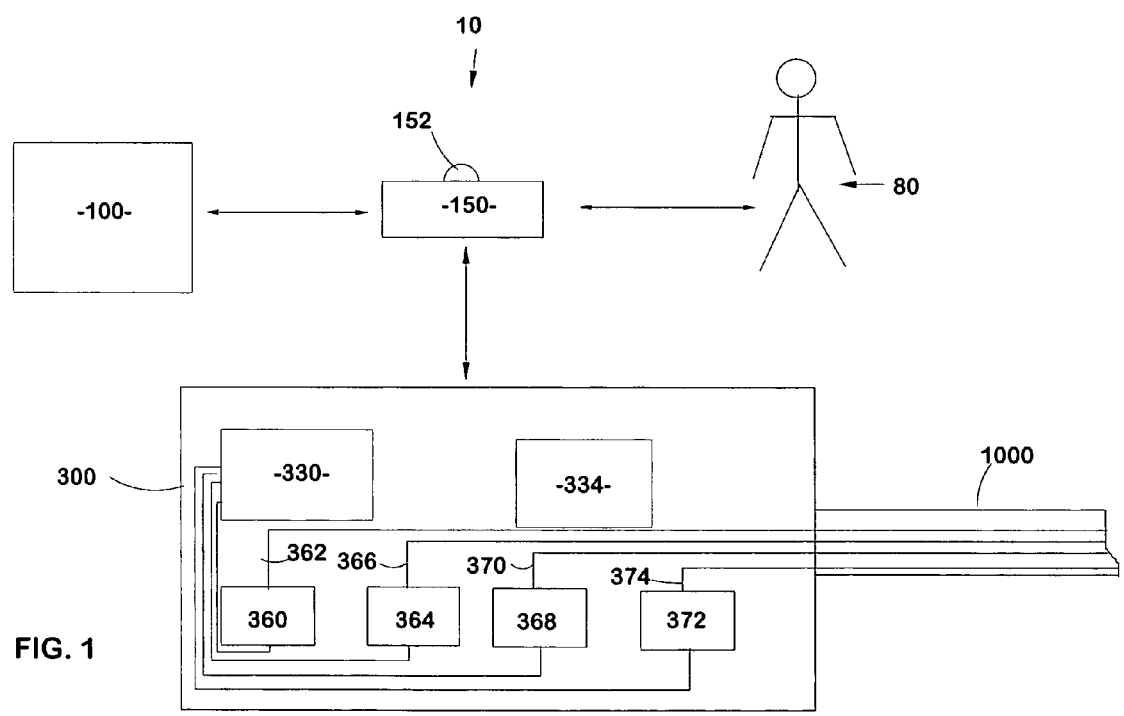
FIG. 1 is a plan view of the architectural design of the disclosed system.

It is advantageous to define several terms before describing the invention. It should be appreciated that the following definitions are used throughout this application.

DEFINITIONS

Where the definition of terms departs from the commonly used meaning of the term, applicant intends to utilize the definitions provided below, unless specifically indicated.

For the purposes of the present invention "stimulation burst width" is the period of time during which a channel is stimulating during a pacing cycle.

For the purposes of the present invention, "C" refers to capacitance.

For the purposes of the present invention, "calibration, calibrate" refers to programming each output channel with a specific $V_{INIT}$ as determined in the characterization process.

For the purposes of the present invention, the term "characterize, characterization" refers to the periodic measurement of capacitor voltage discharged through an electrode-tissue interface in order to determine impedance and depth of discharge as a function of time. This information is then used to determine a channel specific $V_{INIT}$ that will allow the system to deliver the clinician determined stimulation.

For the purposes of the present invention, the term "clinician" refers to any individual who has the ability and access to the programming portion of the system.

For the purposes of the present invention, the term $C_{stim}$ refers to the value of the stimulation or pulse generation capacitor which is a fixed component value based upon manufacturer's labeling.

For the purposes of the present invention, the term $C_{EQ}$ refers to the dynamically calculated parallel capacitance of $C_{stim}$ and $C_{load}$.

For the purposes of the present invention, the term $C_{load}$ refers to the capacitance value of the electrode/tissue interface.

For the purposes of the present invention "channel delay" is set by the clinician and is the programmed period from the beginning of the pacing cycle to the beginning of the start of a stimulation burst on a particular channel.

For purposes of the present invention, "charge and dump" refers to the process of transferring only the needed amount of charge to a capacitor and then discharging the capacitor to the electrode-tissue interface.

For the purposes of the present invention, the term "pacing cycle rate" is measured in CPM and refers to the number of times a single channel completes a stimulation burst within one minute. Only one stimulation burst can be generated per channel per pacing cycle.

For the purposes of the present invention, the term "fractional discharge depth" is the fractional portion of the charge remaining in a capacitor after being discharged from an initial maximum charge for a specific period of time.

For the purposes of the present invention, "electrode tissue interface" refers to the point of contact between the tissue and the electrode.

For the purposes of the present invention, "I" refers to current.

For the purposes of the present invention, "$I_{LOAD}$" refers to the current flowing through the electrode-tissue interface.

For purposes of the present invention, "medical interface" refers to any device used to program the therapeutic parameters required by the system that has the capability of having data entered, changed and saved.

For the purposes of the present invention, the term "multi-channel lead" refers to the flexible, elongated element containing multiple stimulation electrodes.

For the purposes of the present invention, the term "pacing" refers to the application of stimulus for therapeutic benefit.

For the purposes of the present invention "pacing cycle" is one complete sequence of all programmed channels firing.

For the purposes of the present invention "pacing session" is the total time for one clinician programmed therapeutic period.

For the purposes of the present invention, the term "patient" refers to the individual receiving therapy using a multi-channel lead and stimulation control unit.

For the purposes of the present invention, the term "pulse generator" refers to any electronics device or system that produces electrical pulses that invoke therapeutic cellular depolarization for stimulation and/or pacing. In accordance with the disclosed system, the pulse generators may be used in-vivo or externally.

For the purposes of the present invention, "Q" refers to charge.

For the purposes of the present invention, the term "R" refers to resistance.

For the purposes of the present invention, the term "$R_{Load}$" refers to the bulk resistance value of the tissue between the stimulation electrodes dynamically calculated by the system.

For the purposes of the present invention, the term "$R_{EQ}$" refers to the calculated series resistance of $R_{load}$ and $R_{return}$.

For the purposes of the present invention, the term "$R_{return}$" refers to the resistance value used in the output channel ground return path, which is a fixed component value based upon manufacture's labeling.

For the purposes of the present invention, the term "session time" refers the clinician determined period of time stimulation should be delivered to the patient, thereby determining the number of pacing cycles to be completed by the system.

For the purposes of the present invention, the term "stimulation electrodes" refers to electrodes that may be used to transfer energy to the tissue causing cellular depolarization.

For the purposes of the present invention, the term "stimulation" refers to the application of electrical potential causing depolarization of cells.

For the purposes of the present invention, "t" refers to time.

For the purposes of the present invention, "V" refers to voltage.

For the purposes of the present invention, "$Vc_{STIM(EQ)}$" refers to the voltage measured or applied across $C_{STIM(EQ)}$.

For the purposes of the present invention, the term "$V_{init}$" refers to the voltage to which $C_{STIM(EQ)}$ is initialized at the beginning of each stimulation pulse.

For the purposes of the present invention, the term "$V_{MAX}$" refers to the maximum voltage which the system's power source can produce.

For the purposes of the present invention, the term "$V_{RETURN}$" refers to the voltage measured across $R_{RETURN}$.

For the purposes of the present invention, "Z" refers to the impedance of the electrode tissue interface Description In all medical devices embedded with tissue that are powered from a battery, battery life is of a great concern. Although as the battery technology progresses, the lifespan of the batteries increases, researchers are continuing to look for ways to increase battery life, therefore decreasing the frequency of surgery for battery replacement and its inherent risks.

Existing methods for delivering electrical energy to biological tissues for stimulation include constant voltage, constant current and series capacitive charge and dump. In the case of constant voltage or current the electrical energy is down regulated to the desired voltage or current level. The down regulation requires that substantial percentage of the energy stored in the battery be dissipated as heat to achieve the desired stimulation energy. This dissipated energy is non-recoverable and undesirable. The prior art charge and dump is a method of slowly charging a capacitor in series with the electrode-tissue interface and then switching the capacitor in parallel with the electrode-tissue interface to quickly discharge, or dump, the capacitor for stimulation. The charge source for charge and dump is usually a fixed voltage source and power is dissipated in the series current limiting resistor during charging.

In the disclosed invention a stimulation, or pulse generation, capacitor is charged out of circuit from the electrode-tissue interface. The capacitor is charged by a low power dissipation charging circuit to a voltage calculated from the required stimulation current and frequency and the impedance and discharge characteristics of the electrode-tissue interface. The disclosed invention characterizes the electrode-tissue interface prior to the start of each therapeutic pacing session. This enables the device to charge the stimulation capacitors with only the required amount of electrical charge to deliver the required current to the electrode-tissue interface based on the most recent impedance and discharge characteristics of the tissue to be stimulated. This method of delivering only the amount of electric charge needed for stimulation results in an overall saving of energy and an extension of battery life.

The disclosed switched capacitor charge and dump system further reduces energy consumption through the use of multipoint leads. In the disclosed system, each electrode pair in a series requires less charge to stimulate tissue than the prior electrode, thereby saving additional battery life. It has been show that the total energy required to provide effective pacing is significantly less using multiple points of stimulation as compared to single point stimulation.

In the instant invention, only the amount of charge required to produce the desired stimulation is received by the electrodes. This is accomplished through the charge and dump system where the amount of charge required to stimulate the tissue is determined through periodic characterization of the electrode tissue interface. The required charge is stored in a capacitor and then, in a separate action, transferred to the electrode-tissue interface. Although for explanatory purposes only, the following disclosure predominately refers to the gastrointestinal tract, it should be noted that the disclosed system may be used on any portion of a body that requires stimulation or pacing either internally or externally. Examples of uses would be, control of muscle spasticity neural stimulation, cardiac pacing, including tachycardia, bradycardia, demand pacing. The disclosed may also be used for bone healing/repair as well as a means to use electrical current to stimulate bone growth by delivering 10-20 uA of current to the affected bone. This may be done by direct implanted electrodes AC or DC; capacitively coupled through skin electrodes or by electromagnetic fields. In pain management, the disclosed system may be used as a spinal cord and peripheral nerve stimulator to stimulate nerves to block pain sensations from reaching the brain. Other examples would be electrical stimulation to partially restore or enhance function, or movement, (known as Functional Electrical Stimulation) to patients with peripheral nerve and spinal cord damage; deep brain stimulation of the thalamus to relieve debilitating muscle tremors and rigidity caused by Parkinson's disease; sacral nerve stimulation for the treatment of neurogenic incontinence, vagal nerve stimulation for the treatment of epilepsy to reduce seizure occurrence; gastric stimulation for the treatment of gastric motility disorders and retrograde pacing for the treatment of obesity.

The architectural design of the system 10 is illustrated in FIG. 1, consisting of the medical interface 100, telemetry unit 150, pulse generator 300 and multi channel lead 1000. The pulse generator 300 and the multi-channel lead 1000 are, in many applications, embedded within the patent's body 80, although in some applications the pulse generator 300 and multi channel lead may be external to the patient's body. The pulse generator 300 is comprised of a microprocessor 330, wireless communications module 334 and, in this embodiment, four output (4) channels 360, 364, 368 and 372. The microprocessor 330 preferably includes a digital analog converter ("DAC"). Each of the channels 360, 364, 368 and 372 are connected to the microprocessor 330 as known in the art. Channel 360 sends data to the lead 1000 through wire 362; channel 364 sends through wire 366; channel 368 sends through wire 370 and channel 372 sends through wire 374. Each of the wires 362, 366, 370 and 374 are encompassed within the lead 1000 which, as described further herein, contains a pair of electrodes for each of the channels 360, 364, 368 and 372 and their respective wires 362, 366, 370 and 374. Parameters, including but not limited to stimulation amplitude, stimulation burst width, stimulation pulse width, pacing cycle rate, session time, number of channels and channel delay, are transmitted to the pulse generator 300 through use of a telemetry unit 150. The telemetry unit 150 may also have an activation button 152 to enable the patient 80 to activate the system 10. In some embodiments, a real time clock may be incorporated into the pulse generator 300 to enable the microprocessor 330 to send signals to the channels 360, 364, 368 and 372 to initiate a session at preset times in addition to, or rather than, by the patient. Data is passed between the medical interface 100 and the telemetry unit 150 through the use of any hardwire, or wireless connection known in the art. In wireless applications, the telemetry unit 150 may be updated by the medical interface 100 remotely. It should be noted that although channels 360, 364, 368 and 372 are illustrated and referred to herein as separate modules, the microprocessor 330 may operate all operational channels concurrently. Additionally, although four channels have been used as the example for description purposes, this process is applicable to a single channel as well as multiple channels applicable to a specific application, as will be known in the art.

The medical interface 100 enables the clinician to input parameters, as seen in Table I, for stimulation amplitude, stimulation burst width, stimulation pulse width, pacing cycle rate, session time, number of channels and channel delay for each of the four stimulation channels using a PC mouse & keyboard. In one embodiment, the medical interface 100 displays a graphic representation of each stimulation pulse on the monitor. In other embodiments, non-graphical input means may be used to enable the telemetry device 150 to be programmed with telephones or other communication devices without graphic abilities.

In the initial step the clinician creates a patient profile which defines the parameters for the treatment. The example parameters, as seen in Table I, include channel delay, stimulation pulse width, stimulation burst width, stimulation amplitude, pacing rate, channel number and length of treatment session. The parameters illustrated in Table I would be the type used in the explanative description herein relating to the treatment of gastroparesis and parameters applicable to other applications would be evident to those skilled in the medical arts.

As each of the channels may be programmed with its own set of parameters, in one embodiment the number of channels is entered and the parameters repeated for each

TABLE I

| ID | DESCRIPTION | RANGE | RESOLUTION |
| --- | --- | --- | --- |
| $t_{CD}$ | Channel Delay | 0-20 Sec | 0.1 Sec |
| $t_{PW}$ | Stimulation Pulse Width | 0-50 ms | 2 ms |
| $t_{BW}$ | Stimulation Burst Width | 0-2 Sec | 0.1 Sec |
| $I_{STIM}$ | Stimulation Amplitude | 0-4 mA | 0.5 mA |
| $P_{RATE}$ | Pacing Cycle Rate | 2-30 CPM | 1 CPM |
| | Pacing Session | 0-3+ hrs. | 10 minutes |
| | Channel number | 0-4+ | 1 | channel. In another embodiment all channels would automatically have the same parameters and the single setting would affect all channels. Alternatively any number of channels could be programmed to be set together, while the remaining channels are set individually or together. Additionally, any number of channels provided can be used, thereby enabling the clinician to only use one channel on a multichannel lead. How the data entry of the channels is determined would be dependent upon the application and will be evident to those skilled in the art.

When the stimulation profile is complete, the medical clinician downloads the parameters to the telemetry unit 150. The telemetry unit 150 subsequently downloads the parameters into the microprocessor 330 within the pulse generator 300, via wireless transcutaneous communications, thereby providing the microprocessor 330 with the data required to calculate the amount of charge to be transferred to the electrode/tissue interface in order to achieve the clinician determined results.

In order to determine the amount of charge transfer necessary for stimulation, based upon the clinician entered data, the disclosed system periodically characterizes the electrode-tissue interface. To characterize the electrode-tissue interface, the electrical properties including impedance and discharge characteristics of the electrode-tissue interface must be determined.

Figure 2:
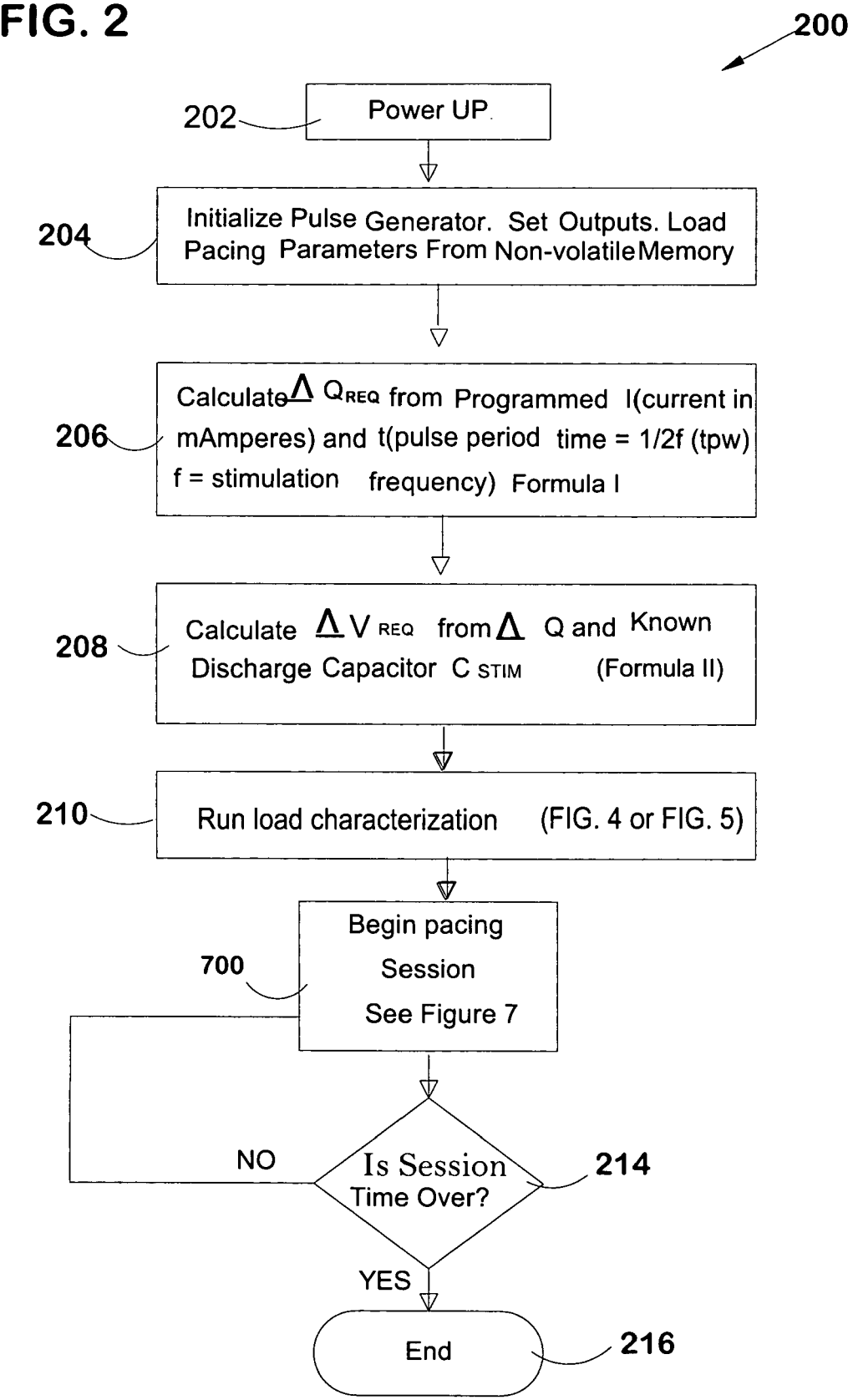
FIG. 2 is a overview flow chart of the system operation.
Figure 4:
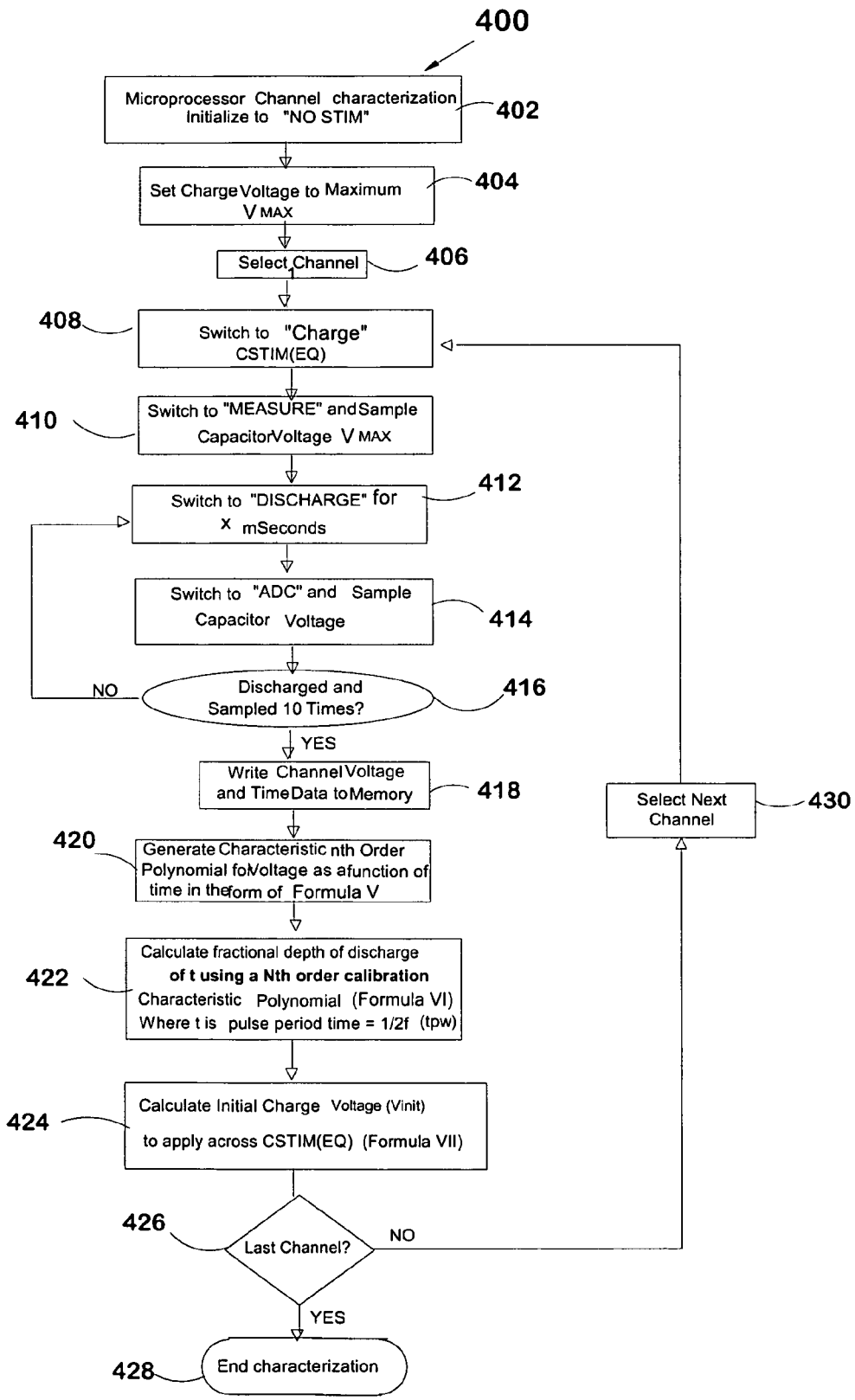
FIG. 4 is a flow chart of the electrode-tissue interface characterization process.
Figure 5:
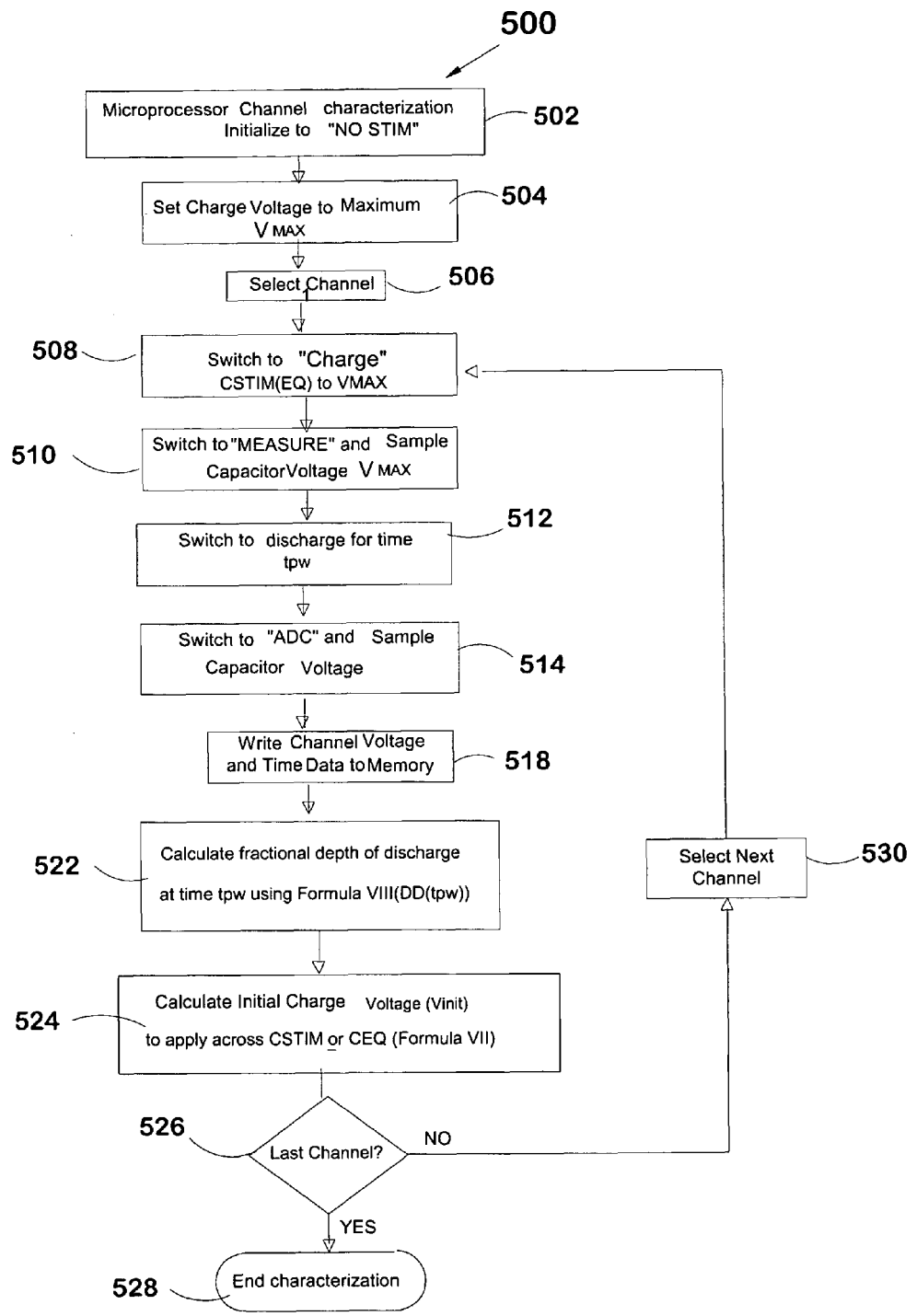
FIG. 5 is a flow chart of an alternate method of characterizing the electrode-tissue interface

An overview of the characterization and pacing process is illustrated in the flow chart 200 of FIG. 2, illustrating the progression from power up 202 to shut down, or end, 216. Once the system is powered up 202, whether it is user or timer initiated, the system loads the parameters from memory 204 and calculates the charge 206 based upon clinician set parameters (see Formula I). The required voltage is then calculated based upon the calculated charge in conjunction with the known value of the capacitor ($C_{STIM}$). Once the voltage and charge are known, the microprocessor 330 initiates the load characterization process 210. The charge voltage for each channel $V_{INIT}$ is calculated in the load characterization process, as illustrated in FIGS. 4 and 5, and when complete the system begins the pacing session 700. At the beginning of the pacing session each channel is calibrated by being programmed with its specific $V_{INIT}$. The stimulation continues on all enabled channels, checking at the end of each pacing cycle whether the session time has expired 214 until the clinician set session time is over 216.

Figure 3A:
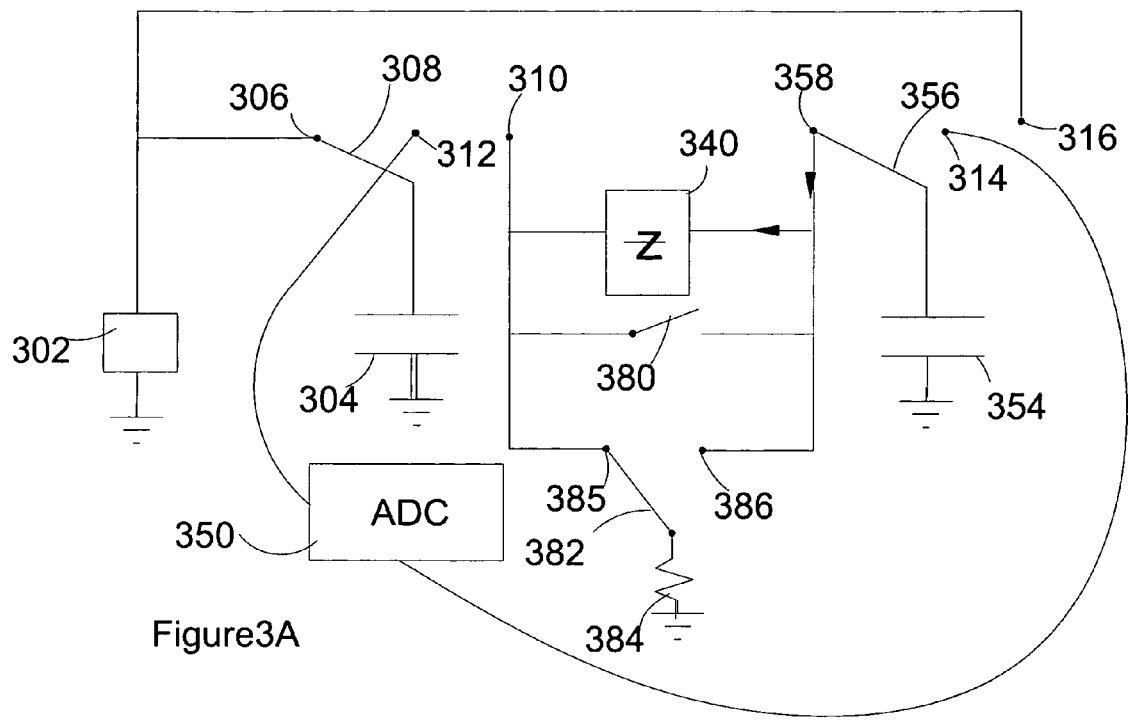
FIG. 3A is a schematic of the disclosed out put channel transferring charge to a first capacitor while a second capacitor is transferring charge through the electrode-tissue interface.
Figure 3B:
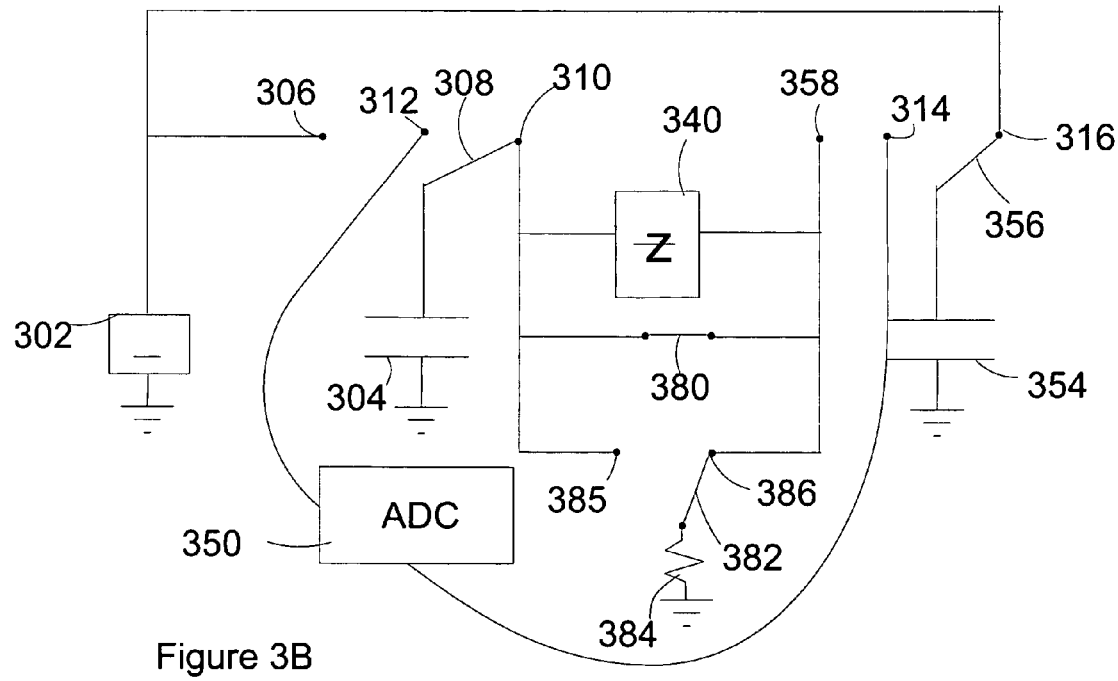
FIG. 3B is a schematic of the disclosed system transferring charge to a second capacitor while the first capacitor is transferring charge through the electrode-tissue interface.

An example of circuitry for use with the disclosed system is illustrated in FIG. 3A and FIG. 3B. The disclosed system has two capacitors 304 and 354 to enable one capacitor 304 or 354 to always be charging while the other capacitor 304 or 354 is transferring charge to the electrode-tissue interface 340 with return switch 382 completing the circuit. This is accomplished through use of switches 308 and 356 which move from charge position at contacts 306 and 316 to charge transfer positions 310 and 358. In these FIG. 3A shows capacitor 304 in the charging position while capacitor 354 is transferring charge to the electrode-tissue interface 340 and 3B shows capacitor 304 transferring charge to the electrode-tissue interface 340 while capacitor 354 is charging. In order to sample the capacitor voltage, an analog digital converter ("ADC") 350 is used, with the switch 308 and 356 connection being made at contacts 312 and 314. The ADC 350 is used to convert the data received from the electrode-tissue interface 340 to digital data readable by the processor 330. The electrode-tissue interface 340 is the point at which the electrodes contact the tissue and serve as the receiving point for the charge. Shorting switch 380 is closed between stimulation bursts and serves to dissipate residual charge at the electrode-tissue interface. In order to simplify explanation of the process, only the process as it relates to capacitor 304 will be described. However it should be noted that whether the capacitor 304 is in charging or transferring charge to the electrode-tissue interface, the capacitor 354 is in the opposite mode.

Calculation Formulas

Formula I

To calculate the charge transfer required to achieve the desired stimulation, $\Delta Q_{REQ}$, as illustrated in the voltage calculation process 206 of flow chart 200, the microprocessor 330 takes the clinician entered required stimulation amplitude ($I_{STIM}$) and required stimulation pulse width ($t_{PW}$)

$$I_{STIM} = \frac{\Delta Q_{REQ}}{t_{PW}}, \text{ alternately } \Delta Q_{REQ} = I_{STIM} \times t_{PW}$$

Formula II

Once the $\Delta Q_{REQ}$ is determined, the system must calculate the required change in voltage 208 ($\Delta V_{REQ}$) across $C_{STIM}$ to transfer the required charge $\Delta Q_{REQ}$ to the tissue. To determine $\Delta V_{REQ}$, the microcontroller 330 uses the above calculated $\Delta Q_{REQ}$ in conjunction with to $C_{STIM}$, the value of which is inherently known as it is part of the stimulation control unit 300.

$$\Delta V_{REQ} = \frac{\Delta Q_{REQ}}{C_{STIM}}$$

Formula III $C_{STIM}$ is simply estimated and constant. For a more accurate calculation of $\Delta V_{REQ}$ the actual parallel equivalent capacitance $C_{EQ}$ of $C_{STIM}$ and load capacitance $C_{LOAD}$ at the electrode/tissue interface should be used. The value for $C_{EQ}$ may be determined dynamically using the following equivalent circuit reduction of the pulse generator channel output and electrode-tissue interface. The equations are used to calculate the value of $C_{EQ}$ from the equivalent circuit model which may be used as an alternative to $C_{STIM}$ in the following formulas to yield more accurate results. In these equations $R_{LOAD}$ is measured dynamically by the device in accordance with Formula IV below.

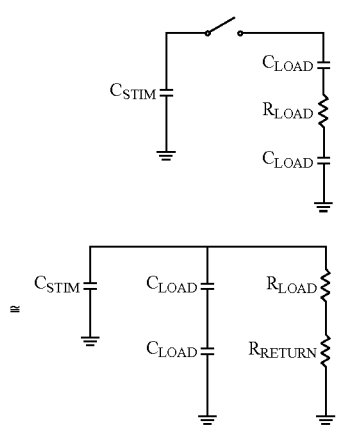

EQ circuit #1

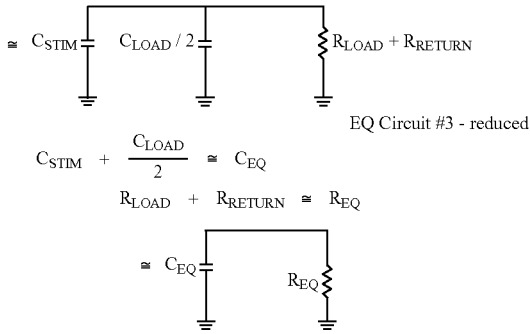

EQ Circuit
Final Reduction $$V_{tpw} = V_0 e^{\frac{-tpw}{R_{EQ}C_{EQ}}}$$

$$\frac{V_{tpw}}{V_0} = e^{\frac{-tpw}{R_{EQ}C_{EQ}}}$$

$$\ln\left(\frac{V_{tpw}}{V_0}\right) = \frac{-tpw}{R_{EQ}C_{EQ}}$$

$$C_{EQ} = \frac{-tpw}{\ln\left(\frac{V_{tpw}}{V_0}\right)R_{EQ}}$$

Once calculated, using Formula III $C_{STIM}$ and $C_{EQ}$ are interchangeable in the following formulas and will be identified as $C_{STIM(EQ)}$ Formula IV $R_{LOAD}$ is measured dynamically by charging, $C_{STIM(EQ)}$ from the power source 302 to maximum voltage, $V_{MAX}$. The charge/discharge switch 308 is then switched to discharge 310 through the electrode/tissue interface 340. Immediately after switching to discharge, the voltage is measured across $R_{RETURN}$ 384 with respect to ground ($V_{RETURN}$) and differential voltage across the electrode/tissue interface 340 ($V_{LOAD}$). The load current $I_{LOAD}$ is then calculated as:

$$I_{LOAD} = \frac{V_{RETURN}}{R_{RETURN}}$$

$$R_{LOAD} = \frac{V_{LOAD}}{I_{LOAD}}$$

The charge discharge switch 308 is then returned to charge position 306.

Once the charge $\Delta Q_{REQ}$ and voltage $\Delta V_{REQ}$ have been determined, the electrode tissue interface is characterized as illustrated in either the flow chart 4 or flow chart 5. The flow chart 5 requires less data manipulation and associated processing time by the microprocessor 330.

It has been found that the percentage of decrease in voltage across $C_{STIM(EQ)}$ for a particular discharge period for a given characterization of the electrode-tissue interface is independent of the initial charge voltage $V_{init}$. This enables the system to periodically recalibrate for changing electrode-tissue conditions and apply the correct therapeutic stimulus. Therefore changes in impedance of the electrode-tissue interface, due to events such as corrosion of the electrodes, dislodging of the electrodes, or changes in the properties of the tissue surrounding the electrodes will not compromise the functionality of the system.

In the method illustrated in FIG. 4 as flow chart 400, the microprocessor 330 commands the charge source 302 in the output channels 360, 364, 368 and 372, to initialize the characterization process 402. Once initiated, the charge voltage across $C_{STIM(EQ)}$ is set to its maximum voltage $V_{MAX}$ 404; the channel is selected 406 and the capacitor 304 is charged to full voltage 408. Once the capacitor 304 is charged, the system samples the capacitor voltage 410 by switching to the analog to ADC 350 by moving the switch 308 to contact 312 to measure the $V_{MAX}$. The capacitor 304 may be charged in any manner known to in the art, such as minimum of five (5) time constants. This charge is then discharged across the electrode tissue interface 340 for a predetermined number of milliseconds 412 by switching switch 308 to position 310. After the predetermined number of milliseconds, the system switches to the ADC 350 by switching switch 308 to contact 312. This enables the ADC to measure 414, and log, the voltage across the capacitor 304. The system continues the discharge/measure process until the capacitor 304 is fully discharged. In the example characterization process flow chart 400, the program designates a discharge and measuring of the capacitor 304 at ten (10) periodic intervals, however this is as an example only and the modification of this, and other commands within the flow chart to equal the same result, will be evident to those skilled in the art. If the voltage $V_{STIM(EQ)}$ across the capacitor 304 has not been measured and discharged for the ten (10) periodic intervals 416, $t_1$, $t_2$, etc. (6A), the system repeats the discharge command 412 until the programmed number of discharges is obtained, or the voltage across $C_{STIM(EQ)}$ is approximately zero.

Figure 6A:
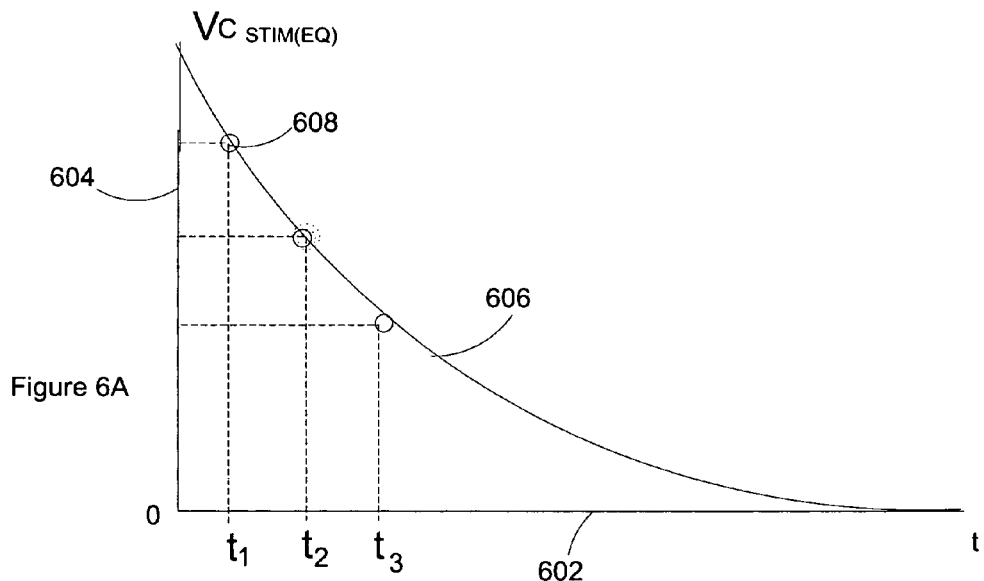
FIG. 6A is a graph of the discharge and measure process for electrode-tissue interface characterization.

Once the capacitor 304 is fully discharged, the system takes the data obtained, saving the data to memory 418, and builds a capacitor discharge curve 606 as illustrated in FIG. 6A. The graph uses the voltage $V_{STIM(EQ)}$ across the capacitor 304 as the y axis 604 and the predetermined discharge time (t) as the x axis 602. The data points 608 are dispersed at regular intervals along the discharge curve 606 based upon the preprogrammed number of samples and the time between samples in accordance with the sequence of FIG. 4. These data are then fit to an equation, such as a $n^{th}$ order polynomial 420, using a regression algorithm, such as Least Squares or an equivalent, where $V_{CAL(t)} = At^3 + Bt^2 + Ct + D$ (Formula V). A third order polynomial is shown here as an example.

Figure 6B:
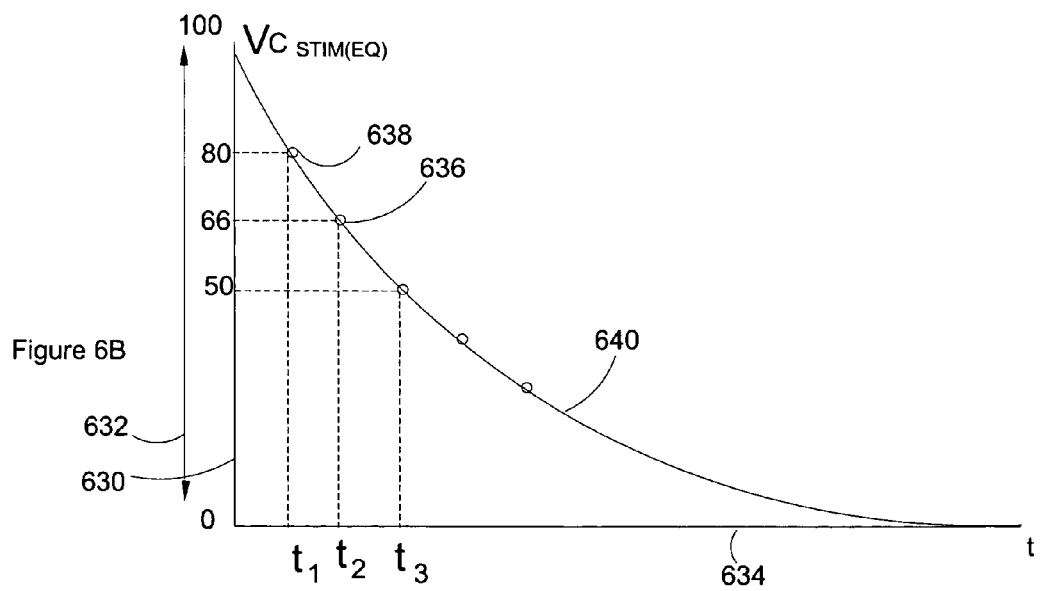
FIG. 6B is a graph of the values of FIG. 6A plotted to determine discharge depth.

Once built, the $n^{th}$ order polynomial $V_{CAL(t)}$ should now be used to calculate the fractional depth of discharge 632 as a function of time along axis 634, using $DD_{(t)} = [V_{CAL(t)}/V_{MAX}]$. (Formula VI) From the example graph of FIG. 6B it may be see that in $t_1$ milliseconds the voltage on $C_{STIM(EQ)}$ which is referred to herein as $Vc_{STIM(EQ)}$ is at the 80% of $V_{MAX}$, data point 638, and $t_2$ is at 66 percent of $V_{MAX}$, data point 636, with each subsequent time data point continuing to decrease. The graph in 6B uses the depth of discharge 632, expressed here as a percentage, as the y axis 630 and the predetermined discharge time (t) as the x axis 634. The data points 638 are dispersed at regular intervals along the discharge curve 640 based upon the preprogrammed number of samples and the time between samples in accordance with the sequence of FIG. 4.

$V_{INIT}$ is then determined by first evaluating the depth of discharge $DD_{(t)}$ for the stimulation pulse width duration $t_{pw}$ and then using $V_{INIT} = [\Delta V_{REQ}/(1-DD_{tpw})]$ (Formula VII). After $V_{INIT}$ for a specific is determined the system then checks whether this is the last channel to be characterized 426. If this is not the last channel, the system selects the next channel 430. When the last channel is reached, the characterization program 400 ends 428.

In the method illustrated in FIG. 5 as flow chart 500, the microprocessor 330 commands the charge source 302 in the output channels 360, 364, 368 and 372, to initialize the characterization process 502. Once initiated, the charge voltage across $C_{STIM(EQ)}$ is set to its maximum voltage $V_{MAX}$ 504; the channel is selected 506 and the capacitor 304 is charged to full voltage 508. Once the capacitor 304 is charged, the system samples the capacitor voltage 510 by switching to the ADC 350 by moving the switch 308 to contact 312 to measure the $V_{MAX}$. The capacitor 304 may be charged in any manner known to in the art, such as minimum of five (5) time constants. This charge is then discharged across the electrode tissue interface 340 for duration $t_{pw}$ 512 by switching switch 308 to position 310. After discharging for $t_{pw}$ milliseconds, the system switches to the ADC 350 by switching switch 308 to contact 312. This enables the ADC to measure 514 the voltage across the capacitor 304, saving the data to memory 518. The fractional depth of discharge is then calculated 522 using $DD_{(tpw)} = V_{(tpw)}/V_{MAX}$ (Formula VIII). Once $DD_{(tpw)}$ is calculated the initial charge voltage $V_{(INIT)}$ is calculated using Formula VII 524. The system then checks to see if this is the last channel 526 to be run. If "yes" the characterization is ended 528 and if "no" the next channel is selected 530.

There are various conditions that will affect the impedance and charge transfer characteristics of the electrode tissue interface. These include:

The type of tissue;
Type of material used to manufacture the pacing leads, e.g. stainless steel, platinum, etc.;
Surface area of electrodes;
Age of electrodes;
Physical connection of electrodes in the tissues, including scar tissue build up; and
Corrosion of the electrodes.

In addition to determining the amount of charge required to meet the clinician set parameters, the stimulation control unit 300 is also capable of providing feedback to the clinician. The system records data such as battery status; patient compliance, including times of use and frequency; impedance changes and errors. Although the system may compensate for a range of impedance variations, there are some instances, such as an electrode torn loose or a broken wire that may cause a dramatic change in impedance at the electrode-tissue interface, where the system cannot compensate by re-running the characterization process. In instances where system generated compensation is impossible, the system may send a warning to the patient indicating that there is a problem. This warning, or notification, would be sent to the telemetry unit 150 where it would be indicated by any visual or audio means convenient for manufacture. Within the range physically possible by the hardware, the clinician may set the degree of acceptable impedance variation based upon the application. For example when the disclosed system is used as a neural stimulator within the brain, the impedance variation may be much narrower than when the system is used in the gastrointestinal tract. Data received from the stimulation control unit 300 may be incorporated into a database maintained by the clinician to enable monitoring of the patient's progress.

The pulse generator 300 controls the stimulation of the electrode pairs 1024A and 1024B, 1026A and 1026B, 1028A and 1028B and 1030A and 1030B as seen in FIG. 10, based upon data received from the telemetry unit 150. Generally the stimulation control unit 300 would activate the electrodes on the multi-channel lead 1002 during updates of operational parameters or when the patient initiates a pacing session, although other activation times may be automatically initiated by the stimulation control unit 300 based upon programming by the clinician. The stimulation control unit 300 controls the pacing stimulation pulse on each of the stimulation channels; with the stimulation parameters of each channel being independently controlled.

Once the parameters are entered, the clinician sends the data to the telemetry unit 150, which encodes the data and sends the encoded data over a wireless connection into the stimulation control unit 300. These programmed stimulation parameters are used to control the timing, duration, direction, sequence and amplitude of each of the utilized output channels by the stimulation control unit 300.

Although the frequency of characterizing the tissue may be programmed to any time periods, tissue is generally characterized at the start of a pacing session. In the treatment of gastroparesis for example the device is turned on one hour before eating, during the meal and runs for two hours after eating. Prior to the start of this therapeutic pacing period the device will characterize the electrode-tissue interface for all enabled channels. The characterization may also be performed if there is a change in parameters by the clinician. Alternatively a real time clock may be added to the embedded system and characterization may be based upon a programmed time schedule. The total session time is a clinician entered parameter as seen in Table I heretofore.

Control of the amount of charge to the capacitors 304 and 354 is accomplished by the charge source 302 by setting $V_{INIT}$ for each channel as determined in the characterization process. As the charge is delivered as a stimulation pulse through the electrode-tissue interface, there is, a positive and a negative. Although either capacitor may deliver the positive and negative charges, for of ease of description herein, capacitor 304 will transfer the positive charge and capacitor 354 will deliver the negative charge.

Figure 7:
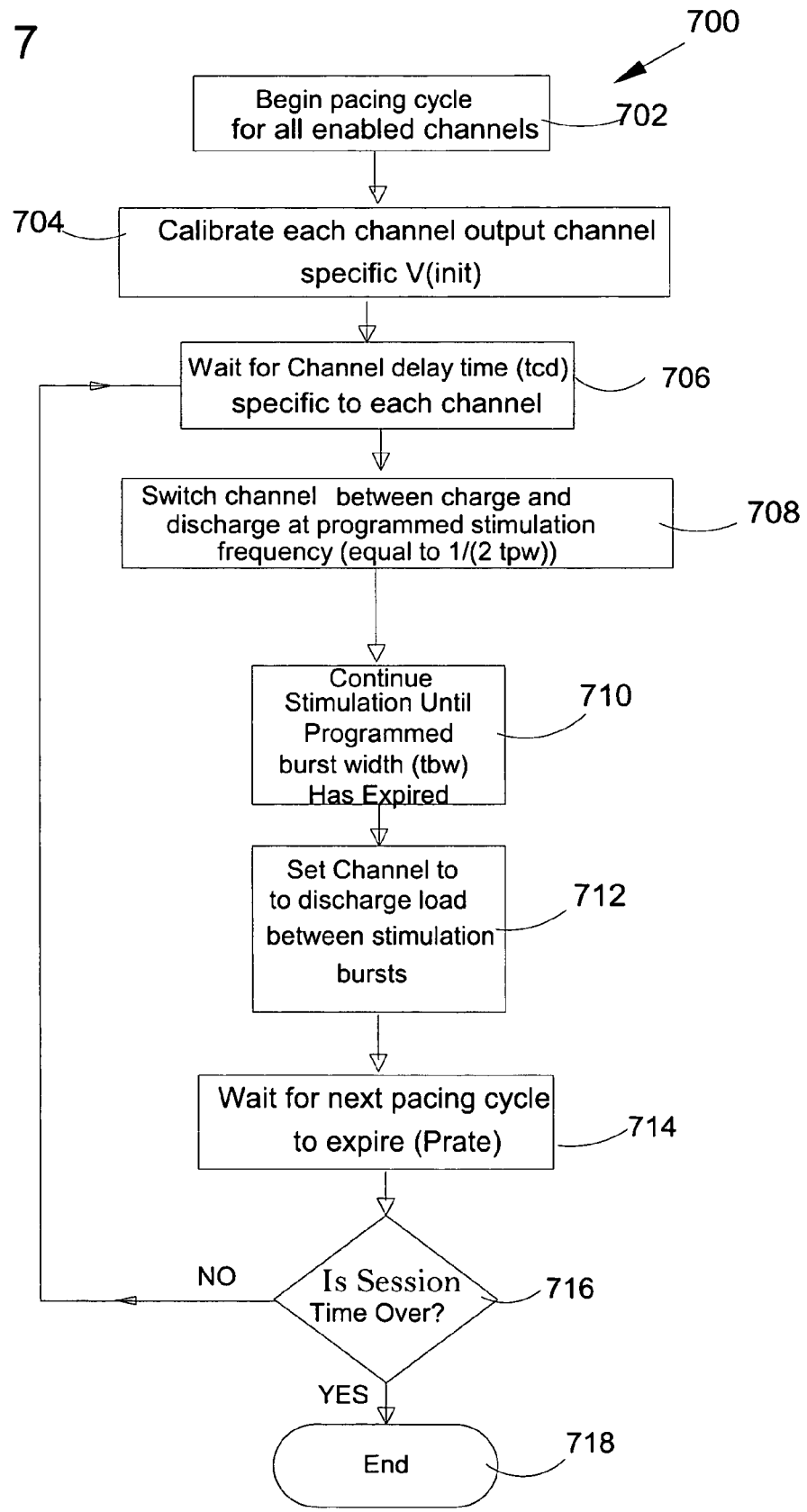
FIG. 7 is a flow chart of the pacing session.

As illustrated in pacing process flow chart 700 of FIG. 7, once the pacing cycle begins, the system selects the parameters set for all enabled channels 702. Each channel is calibrated by being programmed with the specific voltage $V_{INIT}$ which is derived from the electro-tissue interface characterization process. Each channel waits for its specifically programmed channel delay time 707 at which time the stimulation burst is generated 708. Once the stimulation burst duration has expired 710, the system sets the channel shorting switch 380 to discharge the residual charge across the electrode-tissue interface 340. The system then waits for the pacing cycle Prate to expire 714 at which point it checks whether the pacing session has ended 706. If the session has ended 718 the system process ends. If the session has not ended the system waits for the channel specific delay 706, repeating the process until the end of the pacing session.

As shown in FIG. 3A, the stimulation burst is generated as follows. Switch 308 is thrown to contact 306 and switch 356 is thrown to contact 358, thereby enabling the capacitor 304 to charge and capacitor 354 to transfer its charge through the electrode-tissue interface 340. Switch 382 is thrown to contact 385 for this entire state. This state is maintained for the time period $t_{pw}$. As shown in FIG. 3B, which 308 is thrown to position 310 and simultaneously, switch 356 is thrown to contact 360, thereby enabling capacitor 354 to recharge and capacitor 304 to transfer its charge through the electrode tissue interface 340. Switch 382 is thrown to contact 386 for this entire state which is maintained for the time period $t_{pw}$.

This alternating charge and discharge 708 is continued until the stimulation burst width duration has expired 710. Once the stimulation burst width has expired for the current channel, the system checks to see if the pacing session is completed 714. If session is not complete, the system selects the next channel 716, repeating the process until all channels have been stimulated. Once it is determined that the pacing session has expired 714, the session is ended 718.

The disclosed system uses charge balancing to prevent charge build up at the electrode tissue interface 340 and therefore dramatically minimizing corrosion of the stimulation electrodes. One method that the disclosed system uses to achieve charge balancing is generation of a biphasic waveform wherein the capacitors 304 and 354 alternate with equal positive and negative charges.

In addition to the biphasic waveform, the disclosed system uses a shorting switch 380 that discharges any residual charge left at the electrode tissue interface 340 between stimulation bursts. A mismatch between the charge transferred during the positive and the negative stimulation pulses may result in a cumulative residual charge and, by closing the shorting switch 380, as seen in FIG. 3B, any residual charge is discharged at the shorting switch 380, taking the residual charge to zero.

EXAMPLES

Example I

Figure 8A:
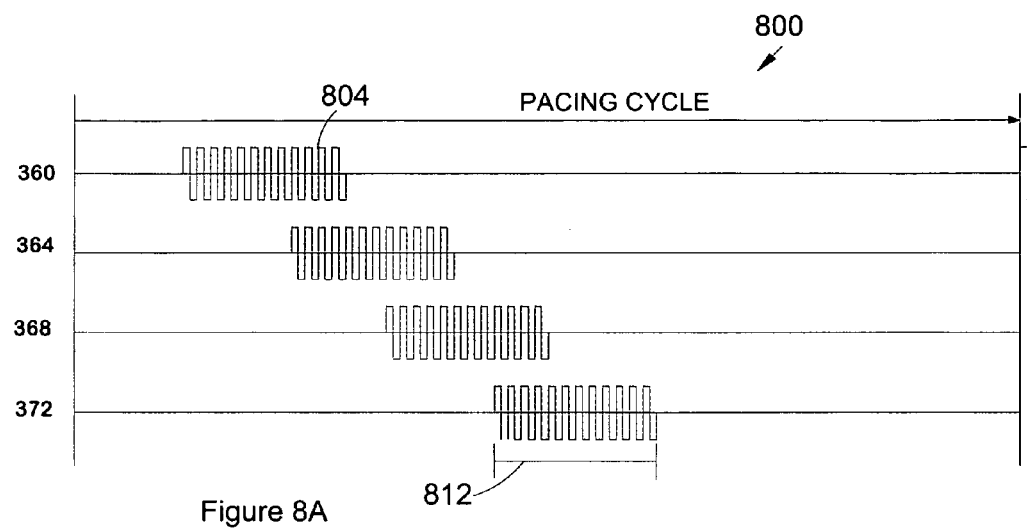
FIG. 8A is a graph illustrating one sequential pacing cycle.

The pacing cycle graph 800 illustrated in FIG. 8A, shows an example of a pacing cycle having four identically programmed channels, thereby creating a protocol where the channel delay time from the initialization of the pacing cycle to the stimulation burst 804 is sequentially longer and the stimulation burst width 812 the same for all of the channels 360, 364, 368 and 372. It should be noted that although the example illustrated in FIG. 8A has four channels, any number of channels may be used that are appropriate for the end application.

Figure 8B:
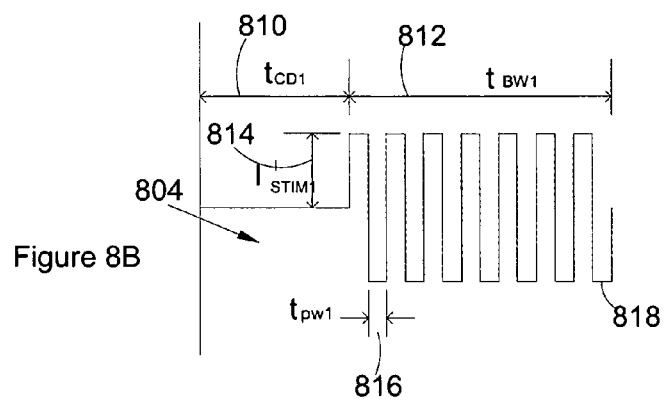
FIG. 8B is a graph illustrating an individual stimulation burst.

In FIG. 8B the stimulation burst 804 for channel 1 360 is shown in detail. The channel delay 810 is the programmed period from the beginning of the pacing cycle to the beginning of the stimulation burst 804. One method of accomplishing this is to start a countdown once the pacing cycle has begun and stopped at the beginning of the stimulation burst 804, although other methods will be evident to those skilled in the art. The stimulation burst width 812, set by the clinician, determines the number of stimulation pulses 818 within each stimulation burst 804 and is defined as a 50% a duty cycle waveform. The stimulation burst width 812 may vary from channel to channel. The stimulation pulse width 816, or alternatively the stimulation frequency, is set by the clinician. The stimulation amplitude 814 is equal to the absolute amplitude of each stimulation pulse relative to zero.

Example III

Figure 9:
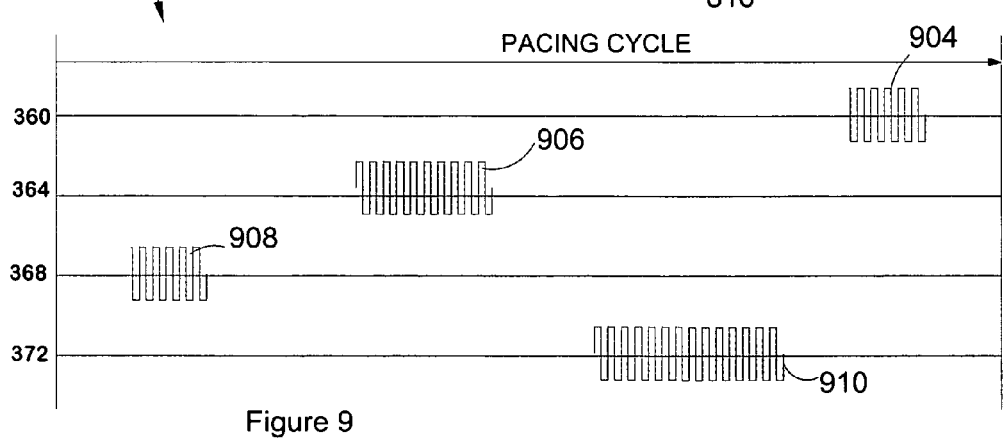
FIG. 9 is a graph illustrating an alternate non-sequential pacing cycle.

The graph 902 illustrated in FIG. 9, shows an example of another pacing protocol where the channel delay is non-sequential for each of the channels 360, 364, 368, 372. Additionally, the stimulation burst width for each of the stimulation bursts differs. In this example the length of the stimulation burst 904 on channel 360 is a first length, stimulation burst 906 on channel 364 a second length, stimulation burst 908 on channel 368 a third length and stimulation burst 910 on channel 372 a fourth length. In this figure the channel stimulation bursts do not overlap. Other examples of customization of the pulsing pattern which may not be illustrated will be known to those skilled in the art and will be dependent upon the application.

An example of a multi-channel lead 1000 is illustrated in FIGS. 10 and 11. In this example the lead 1002 is manufactured from multiple electric conductors encased in a protective flexible polymer, or other bio compatible material, that connects to four pairs of electrodes 1024A and 1024B, 1026A and 1026B, 1028A and 1028B and 1030A and 1030B. Although this embodiment uses a pair of ring electrodes, for example, 1024A and 1024B, any electrode design, configuration and number of electrodes applicable to the application may be used. The stimulation conductors 1008 for each electrode 1024A and 1024B, 1026A and 1026B, 1028A and 1028B and 1030A and 1030B are located within the lead 1002. These wires 1008 may be made from any conductive material having the desired physical properties of low impedance and high flexibility. The electrode wires 1008 are run through the interior of the lead 1002 to the contact points 1014 that are in conductive communication with the control unit 300. The lead 1002 is secured to the patient's body through use of suture anchor cuffs 1010 on either side of the electrode pairs 1024, 1026, 1028 and 1030. The needle (not shown) is used to guide the placement of the pacing lead 1000. The lead 1002 is attached at end 1016 to the needle by a suture and once the lead 1002 is secured in place, the needle is removed.

At the proximal end the lead 1002 is secured to the control unit 300 through the use of a set screw or other applicable securing method at receiving hole 1012. The lead 1002 must be secured to the control unit 300 in a manner to enable the lead contact points 1014 to interact with their counterparts in the control unit 300. At the distal end 1016 of the lead 1002 is the needle attachment point 1018 which is used to attach the lead 1002 to a needle (not shown) for placement in the patient's body in a manner known in the art. The control unit 300 is sutured in a pocket created within the patient's body as known in the art.

As illustrated in this example for gastroparesis, the lead 1002 has electrode pairs 1024, 1026, 1028 and 1030, each having a positive and a negative electrode, with the first electrode ring 1024A being spaced about 1 cm from the second electrode ring 1024B. It should be noted that the spacing between the pairs of electrodes may vary and the appropriate distancing for the specific application will be evident to those skilled in the art. The electrode pairs 1024, 1026, 1028 and 1030 are spaced along the lead about 8 cm from one another in order to allow the electrodes pairs 1024, 1026, 1028 and 1030 to be secured to the patient's stomach about 4 cm apart. The extra 4 cm between the sutured locations of each electrode pair 1024, 1026, 1028 and 1030 permits the lead 1002 to allow for expansion of the patient's stomach. In this example the most distal electrode pair 1024 should be placed at the region of the patient's stomach where the natural gastric slow wave originates. This enables the electrode to more naturally stimulate the appropriate muscles. The exact spacing and placement of the electrodes will be dependent upon the size of the patient and application.

In the embodiment illustrated in FIG. 12, the four electrode pairs 1204 are spaced 4 cm apart and the lead 1202 is secured to the patient, through the use of suture anchor cuffs 1206 on either side of the line of electrode pairs 1204. The proximal end of the lead 1202 has been bifurcated to form lead 1220 and lead 1226. Each of the leads 1220 and 1226 has channel contacts 1222 and 1228 that are connected to the pulse generator 300. This embodiment would be used if the whole electrode section is secured between the cuffs into nonexpanding tissue for stimulation.

Figure 13:
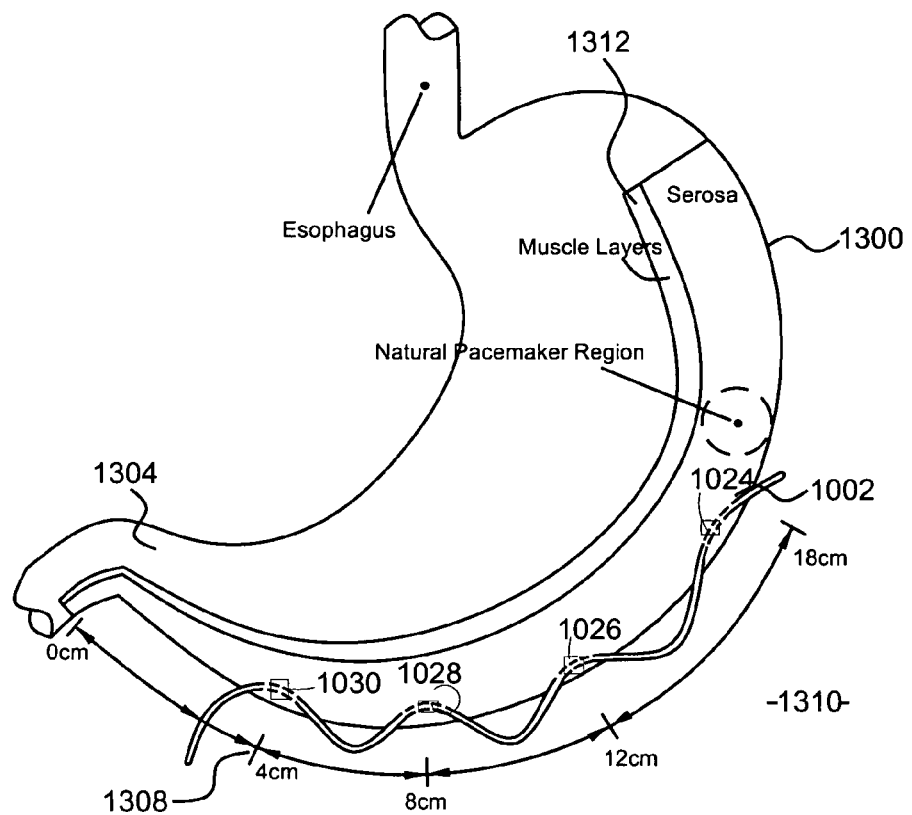
FIG. 13 is a front view of a multi-channel lead within a patient's stomach.
Figure 14:
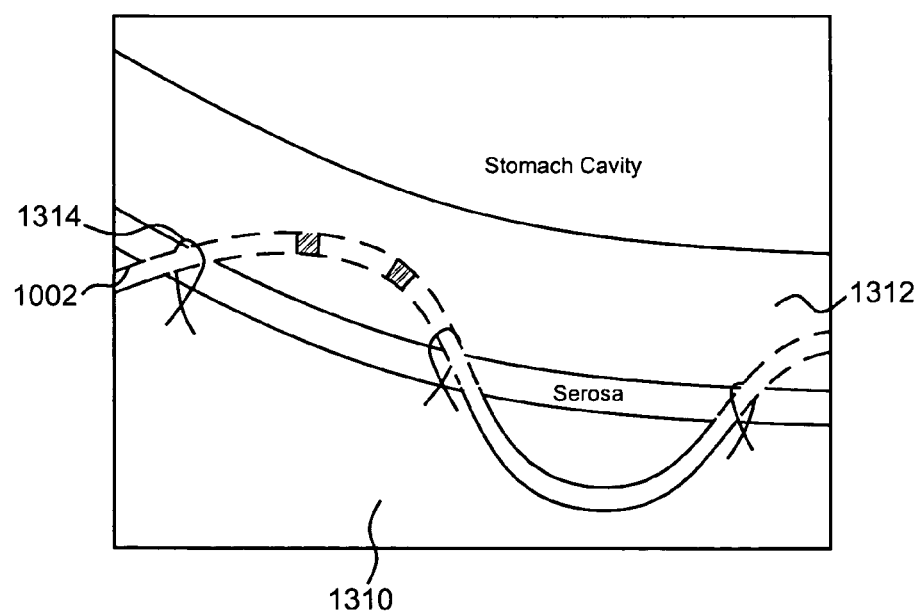
FIG. 14 is a front view of the lead sutured into a patient's stomach.

The lead 1002 is shown in FIGS. 13 and 14 as it would be placed in a patient's stomach 1300 for stimulation of the gastric slow wave to treat gastroparesis. As may be seen in the detailed drawing of FIG. 14, each electrode pair 1024, 1026, 1028 and 1030 is inserted into the stomach muscle tissue 1312 with the excess lead 1002 extending into the abdominal cavity 1310. The first, or distal, electrode pair 1024 is inserted at about 4 cm 1308 from the pylorus 1304. The remaining electrode pairs 1026, 1028 and 1030 are secured to the muscle tissue 1312 at about 4 cm intervals. It should be noted that the distance between the electrode pairs 1024, 1026, 1028 and 1030 is used herein as an example of placement when used for gastroparesis, however the distances may vary dependent upon the patient and application. In FIG. 14, the lead 1002 is shown secured to the muscle tissue 1312 through the use of standard sutures 1314 rather than the suture anchor cuff of FIGS. 10 and 12.

Further reduction in power consumption is achieved by slightly reducing the energy for each channel as the pacing cycle progresses. As seen in the example graph 1500 of FIG. 15, stimulation burst 1502 is at 100% stimulation amplitude, stimulation burst 1504 at 80% stimulation amplitude, stimulation burst 1506 at 60% stimulation amplitude and stimulation burst 1508 at 40% stimulation amplitude.

Figure 15:
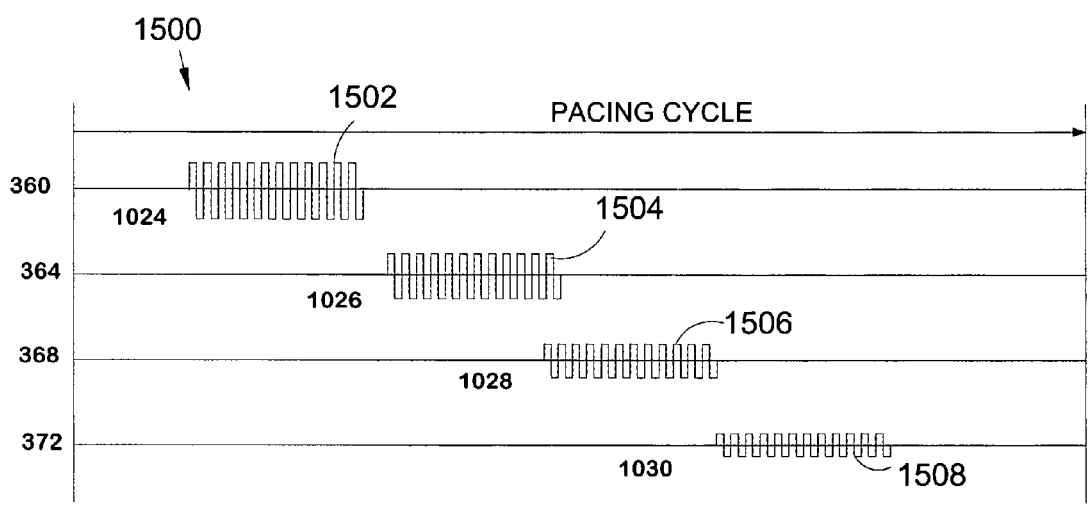
FIG. 15 is a graph of the charge reduction by channel during a pacing cycle.

The reduction in charge is possible as the energy for the stimulation burst 1502 by the most distal electrode pair 1024, with a 100% stimulation, starts the muscle reactions thereby enabling the energy of the subsequent electrode stimulation burst 1504 (electrode pair 1026), on the next channel, to be reduced by 20% while still continuing the momentum. As the muscle momentum continues, the energy for stimulation bursts 1506 (electrode pair 1028) and 1508 (electrode pair 1030) is decreased by 20% each as it is only used to maintain movement. In the example of FIG. 15, the initial stimulation burst 1502 is 2.5 times greater than that of the final stimulation burst 1508. The reduction in energy may be used in any application where the reduction in energy may be beneficial and the applications, in vivo or external, will be evident to those skilled in the art.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method of providing a therapeutic stimulation session, said stimulation session having an initiation, a duration and a termination, comprising the steps of:
   a. performing a load characterization of the electrode-tissue interface at session initiation, using a capacitor having a known capacitance value, to determine an impedance of the electrode-tissue interface and a depth of discharge of the capacitor;
   b. using said load characterization and at least three clinician input parameters, two of said clinician input parameters being stimulation pulse width and the other stimulation amplitude, to determine a required amount of charge to be transferred to said electrode-tissue interface required for stimulation;
   c. determining a required delta voltage by dividing said required amount of charge by the capacitance value of the capacitor; and d. generating multiple identical stimulation pulses with minimal power source consumption for the duration of said stimulation session until said termination.

2. The method of claim 1 wherein performing said load characterization of said electrode-tissue interface includes measuring a decrease in terminal voltage of the capacitor in an initially charged state while discharging through said electrode-tissue interface to measure impedance of the electrode-tissue interface and said depth of discharge of the capacitor as a function of time.

3. The method of claim 2 wherein measuring said depth of discharge of said electrode-tissue interface as a function of time comprises the steps of:
   a. charging the capacitor to a known maximum terminal voltage;
   b. discharging said capacitor through said electrode-tissue interface for a predetermined period of time;
   c. stopping said discharging of said capacitor through said electrode-tissue interface and measuring an open circuit terminal voltage of said capacitor;
   d. repeating steps b. and c. until said capacitor is fully discharged;
   e. creating an equation, using a regression algorithm, from data determined in steps b., c. and d. to represent measured capacitor voltage as a function of time; and
   f. evaluating said equation at said at least one clinician input parameter of stimulation pulse width duration thereby determining said depth of discharge of said capacitor at said stimulation pulse width duration.

4. The method of claim 2 wherein measuring said impedance of the electrode-tissue interface comprises the steps of:
   a. charging a capacitor to a known maximum terminal voltage;
   b. discharging said capacitor through said electrode-tissue interface;
   c. immediately measuring the voltage across said electrode-tissue interface;
   d. immediately measuring the current through said electrode-tissue interface; and
   e. dividing said voltage measured through said electrode-tissue interface by said current measured through said electrode-tissue interface to determine said impedance, said impedance representing the bulk resistance of tissue between said at least one electrode pair.

5. The method of claim 1 wherein said at least one of said at least three clinician input parameters is selected from the group consisting of channel delay, stimulation burst width, pacing cycle rate, pacing session time and channel number.

6. The method of claim 1 further comprising calculating an initial calibration voltage by dividing said required delta voltage by the quantity of 1 minus said depth of discharge of the capacitor, and wherein measuring said depth of discharge of the capacitor comprises the steps of:
   a. charging said capacitor to a known maximum terminal voltage;
   b. discharging said capacitor through said electrode-tissue interface for a predetermined period of time;
   c. stopping said discharging of said capacitor through said electrode-tissue interface and measuring the open circuit terminal voltage of said capacitor;
   d. repeating steps b. and c. until said capacitor is fully discharged;
   e. creating an equation, using a regression algorithm, from data determined in steps b., c. and d. to represent measured capacitor voltage at a function of time; and
   f. evaluating said equation as said at least one clinician input parameter of stimulation pulse width duration to determine said depth of discharge of said capacitor at said stimulation pulse width duration.

7. The method of claim 1 wherein said amount of charge is transferred to said electrode-tissue interface by charging said capacitor to an initial calibration voltage and discharging said capacitor across said electrode-tissue interface for said at least one clinician input parameter of stimulation pulse width duration.

8. The method of claim 1 further comprising a calculation of a second, more accurate required delta voltage comprising the steps of:
   a. performing a load characterization of the electrode-tissue interface to determine an electrode tissue interface capacitance;
   b. determining an equivalent capacitance by combining in parallel the capacitance of said electrode-tissue interface and said known capacitance of said capacitor; and
   c. dividing said required amount of charge by said equivalent capacitance.

* * * * *